United States Patent [19]
Huo et al.

[11] Patent Number: 6,093,403
[45] Date of Patent: Jul. 25, 2000

[54] SUGAR IMBALANCE AND DIABETES TREATING HERBAL FORMULATION

[75] Inventors: Yu Shu Huo, Dalian, China; Sou Jen Lo, Taipei, Taiwan; Wendell D. Winters, San Antonio, Tex.

[73] Assignee: Phytocell Research, Inc., San Antonio, Tex.

[21] Appl. No.: 09/257,842

[22] Filed: Feb. 25, 1999

Related U.S. Application Data

[63] Continuation-in-part of application No. 08/905,209, Aug. 1, 1997, abandoned.

[51] Int. Cl.$^7$ .............................. A61K 35/78; A23L 1/30
[52] U.S. Cl. ....................... 424/195.1; 424/439; 424/441; 426/481; 426/489; 426/648; 426/655; 514/866; 514/909
[58] Field of Search ...................... 424/439, 441, 424/195.1; 426/648, 655, 489, 481; 514/866, 909

[56] References Cited

U.S. PATENT DOCUMENTS

| | | | |
|---|---|---|---|
| 5,595,743 | 1/1997 | Wu | 424/195.1 |
| 5,614,224 | 3/1997 | Womack | 424/646 |
| 5,776,460 | 7/1998 | Kim et al. | 424/195.1 |

FOREIGN PATENT DOCUMENTS

| | | |
|---|---|---|
| 9176019 | 7/1997 | Japan . |

OTHER PUBLICATIONS

Nakajima et al. Phytochem. vol. 36 (1), pp. 119–127, 1994.
Tyler, V. Herbs of Choice, pp. 171–174, 1994.
PDR for Herbal Medicines, p. 1009, 1998.

*Primary Examiner*—Leon B. Lankford, Jr.
*Assistant Examiner*—Christopher R. Tate
*Attorney, Agent, or Firm*—Gray Cary Ware & Freidenrich LLP; Stephen E. Reiter; Ramsey R. Stewart

[57] ABSTRACT

An herbal formulation is disclosed for treating and preventing non-insulin dependent diabetes mellitus (NIDDM) and other sugar imbalances. The herbal formulation is added to the diet of a person suffering from NIDDM in a lectin mixture containing the herbal formulation. The herbal formulation lowers the blood glucose and insulin levels. Adding the herbal formulation to the diet of persons who are in high risk of suffering from NIDDM has a significant effect on lowering blood glucose and insulin levels. Repeated doses of the herbal formulation in a lectin mixture will bring the blood glucose and insulin levels into a desired range. The herbal formulation is made from plant extracts and is useful in the prevention and treatment of sugar imbalances.

19 Claims, 7 Drawing Sheets

SUGAR IMBALANCE AND DIABETES TREATING HERBAL FORMULATION

This application is a Continuation In Part of application Ser. No. 08/905,209 filed Aug. 1, 1997, now abandoned.

BACKGROUND OF THE INVENTION

1. Field of the Invention

This invention relates to the prevention and treatment of non-insulin dependent diabetes mellitus (NIDDM) using a herbal formulation of plant extracts containing lectins and lectin-like compounds.

2. Brief Description of the Prior Art

The use of plant extracts and derivatives of plants for healing and prevention purposes has been described extensively in traditional and folk medicine literature. Over the centuries, plants have served as a major source of medicines for treating and prevention of diseases of mankind. Although recently the ability for synthesis and design of new medicines has provided new pathways for the development of therapeutic drugs, drug medicines derived from plants (phytomedicines) still have a very solid position in drugs used today. Phytomedicines are used in traditional and folk medicines by over 80 percent of the population in developing countries. In the United States, a $12 billion market has developed for plant derived medications, some of which are part of the established medical community and some of which are part of a community referred to as folk medicine.

For centuries, extracts and derivatives of specific plants or mixtures thereof have been used for treatment of illnesses. Many of these extracts or derivatives have been documented as having clinical effectiveness in treating illnesses. One such example is the aloe vera plant which is used in treating burns, minor cuts, and scratches.

Some extracts and components have been found useful in the treatment of sugar imbalances in diabetes. Other extracts and derivatives have been found effective in treating water retention problems that often accompany diabetes. The herbals listed in the following Table 1 are known to be prescribed for the treatment of diabetes.

TABLE 1

Number of Times Herbal was Used in Relation to NIDDM
(From the Original Chinese Literature and Translations Into English)
(Current to November 1996)

| HERBAL | TIMES USED IN 28 PRESCRIPTIONS OF CHINESE TRADITIONAL MEDICINE FROM 1980 1990 | TIMES USED IN 30 PRESCRIPTIONS OF CHINESE TRADITIONAL MEDICINE FROM 1990 1994 |
| --- | --- | --- |
| Radix Rehmanniae | 18 | 13 |
| Radix Astragali | 16 | 10 |
| Radix Ginseng | 16 | 10 |
| Rhizoma Dioscoreae | 12 | 9 |
| Fructus Schisandrae | 11 | 3 |
| Radix Trichosanthis | 10 | 4 |
| Radix Puerariae | 6 | 4 |
| Fructus Lycii | 6 | 3 |
| Poria | 5 | 5 |
| Rhizoma Coptidis |  | 4 |
| Radix Glycyrrhizae |  | 4 |

Dr. Sou Jen Lo, a co-inventor in this application, has been making and selling an herbal formula in Taiwan and southern China that is used to provide relief from symptoms of the water retention which often accompanies diabetes. The herbal formula by Dr. Lo is composed of the following ingredients in the relative amounts listed in table 2.

TABLE 2

| INGREDIENT | AMOUNT BY WEIGHT |
| --- | --- |
| Radix Ginseng | 300 grams |
| Radix Puerariae | 450 grams |
| Radix Scutellariae | 300 grams |
| Radix Ophiopogonis | 300 grams |
| Poria | 300 grams |
| Rhizoma Coptidis | 300 grams |
| Rhizoma Dioscoreae | 300 grams |
| Radix Trichosanthis | 450 grams |
| Radix Glycyrrhizae | 150 grams |
| Radix Astragali | 150 grams |
| Mixture Powder Total | 3,000 grams |

Dr. Yu Shu Huo, another co-inventor in this application, was a physician in rural areas of China. For many years his practice relied on herbal medicines, because of its remote locale. One of the herbal formulas sold by Dr. Huo was used to provide relief from diabetic symptoms. This herbal formula, called "Shenqi Jiangtang Keli", was composed of the following ingredients in the relative amounts listed in table 3.

TABLE 3

| INGREDIENTS | AMOUNT BY WEIGHT |
| --- | --- |
| Radix Ginseng | 480 milligrams |
| Radix Rehmanniae | 480 milligrams |
| Radix Scutellariae | 360 milligrams |
| Radix Ophiopogonis | 360 milligrams |
| Poria | 240 milligrams |
| Radix Astragali | 360 milligrams |
| Radix Puerariae | 360 milligrams |
| Rhizoma Coptidis | 180 milligrams |
| Radix Glycyrrhizae | 180 milligrams |
| Each Bag (3 gram) Total | 3,000 milligram (3 grams) |

Neither of these herbal mixtures were found to be as effective as the new mixture of the present invention. Further, neither prior mixture was found to be as effective in controlling weight, a common problem among diabetics.

SUMMARY OF THE INVENTION

It is an object of the present invention to provide a unique herbal formula that may be used as a dietary supplement to control weight.

It is a further object of the present invention to provide an herbal formula that may be used in the prevention and treatment of sugar imbalances.

It is yet another object of the present invention to provide an herbal formulation that may be used in treating diabetes mellitus.

It is still another object of the present invention to provide an herbal formula that may be used in preventing and treating non-insulin dependent diabetes mellitus and other sugar imbalances.

It is yet another object of the present invention to provide an herbal formulation that is effective in lowering blood glucose and insulin levels in diabetics.

The herbal formulations are composed of a series of herbal ingredients in unique amounts that may be used to either prevent or treat diabetic conditions. Controlled lab experiments have established that the herbal mixtures work as indicated. The results of these experiments were so surprising that the Food and Drug Administration, upon learning of the results, has encouraged the inventors to proceed with additional experiments. Further, the Food and Drug Administration is currently considering the herbal mixture of the present invention for its orphan drug program, the testing of which is subsidized by the government.

DESCRIPTION OF THE PREFERRED EMBODIMENT

Figure 1:
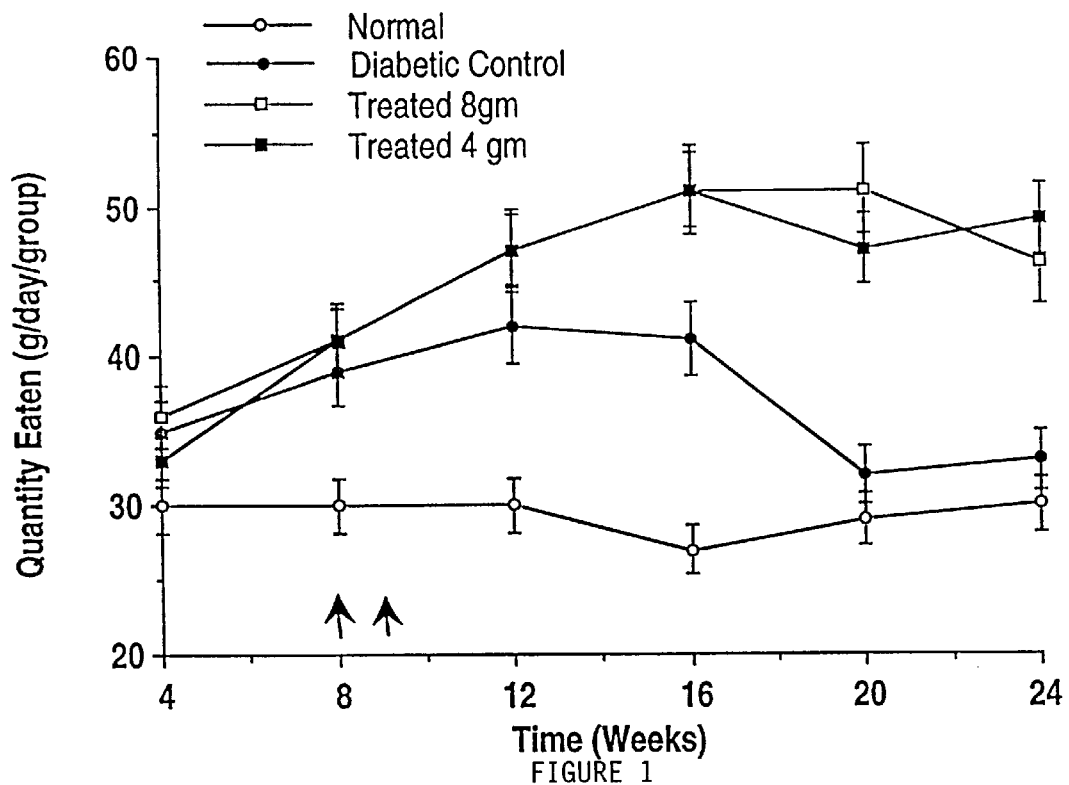
FIG. 1 is a chart representing food consumption by mice during treatment trials.

Problems of sugar imbalance and glucose level fluctuation are associated with diabetes. Severe diabetic conditions require the taking of insulin and other treatment to maintain a safe level of sugar in the blood. One form of diabetes is known as "diabetes mellitus" which is a metabolic disorder arising from a defect in carbohydrate utilization by the body. The problem stems from inadequate or abnormal insulin production by the pancreas.

The inventors have discovered that extracts prepared from leaf and root portions of several types of plants have a marked and significant effect in the (a) prevention and (b) treatment of sugar imbalances. The ingredients were applied to the diet of both animals and humans and found to be effective for non-insulin dependent diabetes mellitus (NIDDM). The ingredients, which comprise the herbal mixture, have also been shown to be effective when used as special supplements to diets during long-term feeding studies in diet induced NIDDM animal models. The extracts have also been found to be effective in long-term studies involving human NIDDM patients, some of whom may receive anti-diabetes drugs while others may not.

The phytoconstituents in the extracts are contained in a lectin-rich compound of plant extracts that may include commonly ingested natural sugars. While the phytoconstituents may be prepared a number of different ways, the recommended way of preparation is extraction by boiling in water in a manner that will be described subsequently. Commonly used solvents that may prepare other extracts are not used in preparing the phytoconstituents used in the present invention. Such solvents include acetone, alcohols, ethoacetate, or glycerine.

Applicants have found that fully dried plant materials are the best for boiling in water for the extraction process. The active compounds can be identified in those extracts by hemagglutination assays.

The herbal formulation of the present invention is prepared from leaf and root portions of several specific types of plants that have a marked and significant effect in the prevention and treatment of sugar imbalances. Experiments were conducted in light of the formulations indicated in tables 2 and 3. Other formulations and herbals, including many of those indicated in table 1, were also examined. Following experimentation, the preferred ingredient mixture indicated in table 4 was derived.

TABLE 4

Preferred Embodiment

| INGREDIENT | WEIGHT | PERCENT |
| --- | --- | --- |
| Radix Ginseng | 250 g | 10% |
| Radix Rehmanniae | 250 g | 10% |
| Radix Ophiopogonis | 200 g | 8% |
| Fructus Schisandrae | 200 g | 8% |
| Rhizoma Dioscoreae | 200 g | 8% |
| Radix Astragali | 200 g | 8% |
| Radix Trichosanthis | 200 g | 8% |
| Radix Puerariae | 200 g | 8% |
| Fructus Lycii | 200 g | 8% |
| Sclerotium Poria Cocos | 150 g | 6% |
| Rhizoma Alismatis | 150 g | 6% |
| Rhizoma Coptidis | 100 g | 4% |
| Fructus Rubi | 100 g | 4% |
| Radix Scutellariae | 50 g | 2% |
| Radix Glycyrrhizae | 50 g | 2% |
| Total | 2,500 g | 100% |

A definition of the various ingredients is provided hereinbelow.

Radix Trichosanthis is from the plant family known as Cucurbitaceae. It is used as the dried root of *Trichosanthes kirilowii* Maxim. The root is collected in the fall and winter as it grows in southern China.

Sclerotium Poria Cocos is from the plant family known as Polyporaceae. It is used as the dried sclerotium (hard fibers) of *Poria cocos* (Schw.) Wolf. The hard fibers are collected throughout the year as it grows in middle china.

Radix Ophiopogonis is from the plant family known as Liliaceae. It is used as the dried root of *Ophiopoqon japonicus* (Thunb.) Ker-Gawl. The root is collected in the autumn as it grows in middle China.

Radix Rehmanniae is from the plant family known as Scrophulariaceae. It is used as the dried root of *Rehmanniae glutinosa* (Libosch). It is collected in the spring and fall as it is grown in southern China.

Radix Puerariae is from the plant family known as Leguminosae. It is used as the dried root of *Pueraria lobata* (Willd.) Ohwi. It is collected in the fall and winter as it grows in middle and northern China.

Rhizoma Dioscoreae is from the plant family known as Dioscoreaceae. It is used as the dried rhizome of *Dioscorea opposita* (Thunb.). It is collected in the winter as it grows in middle and northern China.

Radix Astragali is from the plant family known as Leguminosae. It is used as the dried root of *Astragalus membranaceus* (Fisch.) Bge. It is collected in autumn from northern China regions.

Rhizoma Alismatis is from the plant family known as Alismataceae. It is used as the dried rhizome of *Alisma orientalis* (Sam) Juzep. It is collected during the year where it grows in middle and southern China.

Fructus Rubi is from the plant family known as Rosaceae. It is used as the dried fruit of *Rubus chingii* Hu. It is collected in the spring and fall from middle and southern China.

Radix Ginseng is from the plant family Araliaceae known as Panax. It is used as the dried root of *Panax ginseng* C. A. Meyer. It is collected in the summer and fall as it grows in the tropical regions, i.e. northeastern, of China.

Rhizoma Coptidis is from the plant family known as Ranunculaceae. It is used as the dried Rhizome of *Coptis chinensis* Franch. It is collected in the fall as it grows in middle and northern China.

Radix Glycyrrhizae is from the plant family known as Leguminosae. It is used as the dried root and dried rhizome of *Glycyrrhiza uralensis* Fisch. It is collected in the spring and fall as it grows in the Inner Mongolian areas of China.

Radix Scutellariae is from the plant family known as Labiatae. It is used as the dried root of *Scutellaria baicalensis* Georgi. It is collected in the spring and the fall as it grows in middle and northern China.

Fructus Schisandrae is from the plant family known as Magnoliaceae. It is used as the dried fruit of *Schisandra chinensis* (Turcz). It is collected in the autumn as it grows in the Inner Mongolian and northeast regions of China.

Fructus Lycii is from the plant family known as Solanaceae. It is used as the fruit of *Lycium bararum L*. It is collected in the autumn as it grows in northwest regions of China.

Of the individual herbs listed above, only the finest are selected at the best sites of growth and collected from the fields at the correct time of harvest on the basis of maturity, age, nutrition, and appearance. Medical herbal specialists are used to select the individual herbs at the time of collection.

Each of the individual herbs in the formula, whether collected as leaves, roots, or grains, are sliced and dried. The preferred embodiment formula is made in two parts and are then combined in a third part as described hereinbelow.

Part 1: Extracts

During part one of the process, the essential dried herbals of Radix Trichosanthis (approximately 200 grams), Fructus Lycii (approximately 200 grams), Radix Rehmanniae (approximately 250 grams), Radix Astragali (approximately 200 grams), Rhizoma Alismatis (approximately 150 grams), and Fructus Rubi (approximately 100 grams) are all individually washed three times in water and then cut into small pieces. Sclerotium Poria Cocos (approximately 150 grams), Fructus Schisandrae (approximately 200 grams), Radix Ophiopogonis (approximately 200 grams), Rhizoma Dioscoreae (approximately 200 grams) may also be treated in this manner. These dried cut herbals are added to sterile water at room temperature and heated over six hours at 100 degrees C. The quantity of water is five times that of the mixture of the herbals. The mixture is then boiled for four hours. The water is then extracted and saved and fresh water is added and the mixture of herbals is again boiled for four hours and a second extraction of water is save.

The first and second extraction of water is combined and passed through a G-4 filter. The filtered extract is then pumped in the form of a high pressure spray into a vacuum tank and incubated at 80 degrees C. The solid particles contained in the extract settle down to the bottom of the tank and, as the liquid evaporates, remains as a dry powder. Out of 1,800 grams of herbals used in the part one extraction process, approximately 400 grams of dry powder will remain.

Part 2: Mixed Powders

The essential dried herbal of Radix Ginseng (approximately 250 grams) is washed three times in water and then cut into small pieces. Radix Puerariae (approximately 200 grams), Radix Glycyrrhizae (approximately 50 grams), Radix Scutellariae (approximately 50 grams), and Rhizoma Coptidis (approximately 100 grams) may also be treated in this manner. The small pieces are mixed together, pulverized, and milled together. They may be remilled if a finer mixture is needed.

The milled powder mixture has been screened through a 100 fine screen. Approximately 90 percent of the materials or 630 grams out of a starting 700 grams will remain.

Part 3: Preparing Final Product

The powdered extract from Part 1 and the screened milled mixed powders of Part 2 are then mixed together in an agitator/mixer. The mixed powders of the completed formula are dry heat sterilized in the air. After the dry heat sterilization, the completed formula is dispensed into sterile bags of 1000 grams each.

In this process, it is important that additional items are not added. Particularly no fillers, extenders, lubricants, perfumes, dyes, preservatives, or any other chemicals are added at any step. The substance that is left is an entirely herbal mixture prepared from the herbs indicated in the preferred formula.

Range of Variation

The individual ingredient amounts may be cut in half or be increased twofold. For example, Radix Trichosanthis could have as little as 100 grams or as much as 400 grams. The range of variation in individual herbal amounts is depicted in table 5 here.

TABLE 5

Preferred Embodiment Ingredient Ranges

| INGREDIENT | WEIGHT | PERCENT |
| --- | --- | --- |
| Radix Ginseng | 125–500 g | 5–20% |
| Radix Rehmanniae | 125–500 g | 5–20% |
| Radix Ophiopogonis | 100–400 g | 4–16% |
| Fructus Schisandrae | 100–400 g | 4–16% |
| Rhizoma Dioscoreae | 100–400 g | 4–16% |
| Radix Astragali | 100–400 g | 4–16% |
| Radix Trichosanthis | 100–400 g | 4–16% |
| Radix Puerariae | 100–400 g | 4–16% |
| Fructus Lycii | 100–400 g | 4–16% |
| Sclerotium Poria Cocos | 75–300 g | 3–12% |
| Rhizoma Alismatis | 75–300 g | 3–12% |
| Rhizoma Coptidis | 50–200 g | 2–8% |
| Fructus Rubi | 50–200 g | 2–8% |
| Radix Scutellariae | 25–100 g | 1–4% |
| Radix Glycyrrhizae | 25–100 g | 1–4% |

To determine the effectiveness of the herbal formula, the inventors have conducted both in vivo and in vitro experiments. In the in vivo experiments, the inventors discovered that the formula for the present invention would significantly reduce serum glucose and insulin levels, body weight, and insulin resistance during control studies of treatment and prevention of non-insulin dependent diabetes mellitus (NIDDM). The experiment made use of a mouse model well recognized in the art as inducing NIDDM through diet.

In both the treatment and prevention trials described hereinbelow, similar protocols and methods were used in animal care and to measure the bio-responses of the animals.

In Vivo Studies—Treatment Trials

A total of 40 male mice were used in these experiments. Weaning age mice were randomly put in four groups of ten mice each and given the designation of (1) Normal, (2) Diabetic Control, (3) Treatment 8, and (4) Treatment 4. The Normal group of mice were thereafter fed a normal mouse diet.

The other three groups were thereafter fed a diabetes inducing diet consisting of high fat, high simple sugar, low fiber diet. At the time of diagnosis of diabetic levels of blood sugar in the three groups of mice fed the diabetes inducing diet (typically 8 to 9 weeks from the start), the Treatment 4 group was thereafter fed four grams per day per mouse of the present invention mixed into the induction food. The Treatment 8 group were thereafter fed 8 grams per day per mouse of the present invention mixed into the induction food. The remaining group remained as the Diabetes Control group.

Measurements of the mice in each group were performed at the end of 4, 8, 12, 16, 20, and 24 weeks from the start of the special diet. Items measured for each mouse in the different groups at each of the intervals was food consumption, body weight, and blood glucose levels. At the end of 24 weeks, serum insulin and insulin resistance were also measured.

In Vivo Studies—Prevention Trials

A total of 40 male mice were used in these experiments. Mice at weaning age were randomly put into four groups of ten mice each and designated (1) Normal, (2) Diabetic Control, (3) Treatment 8, and (4) Treatment 4. Beginning at this time, the Normal group of mice were thereafter fed a normal mouse chow.

Of the remaining three groups, they were fed a diabetes induction diet consisting of high fat, high simple sugar, and low fiber foods. Treatment 4 group was fed four grams per day per mouse of the present invention mixed into a diabetes induction food. The Treatment 8 group was fed eight grams per day per mouse of the present invention along with the diabetes induction food.

Measurements of the mice in each group were performed at the end of 4, 8, 12, 16, 20, and 24 weeks from the start. Items measured in each mouse at each interval was food consumption, body weight, and blood glucose level. At the end of the 24 weeks, serum insulin and insulin resistance were also determined.

In the in vivo experiments, the inventors discovered the presence of lectin-like agglutinins in extracts of the formula of our present invention. This was demonstrated by quantitative agglutination assays using human red blood cells (hemagglutination assays (HA)). Additional hemagglutination assays performed using extracts of two commercially available formulas, which have been used for many years for diabetes associated symptoms (Formula One and Formula Two), show the presence of lectin-like agglutinates. HA titers of ten separate extracts of Formula One average 1:8 and those of 12 separate extracts of Formula Two average 1:4. Assays of 15 separate extracts of the formula of the present invention prepared in 1995 and of 18 extracts prepared in 1996 showed HA titers of 1:16. Therefore, lectin-like agglutinates were present in extracts of the formula of the present invention and in Formula's One and Two. The titers were two to four times higher in extracts of the present formula.

To establish specificity and sensitivity of the lectin-like agglutinates in the extract of the formula of the present invention, the inventors used sugar binding hemagglutination assays in which 13 reference sugars ranging from simple sugars to disaccharides were ultimately tested for bindings of extracts of the present formula. Results of the study showed that while extracts of the present formula and extracts of the old Formulas One and Two showed the presence of agglutinates with similar sugars, the level (titers) of specific sugar bindings of hemagglutination were specifically and markedly higher for all of the reactive reference sugars tested using extract of the present formula.

In Vivo Studies—Treatment Trial Results

Some figures indicating the measurements taken of the different groups of mice in the in vivo studies--treatment trials is described hereinbelow. FIG. 1 shows the pattern of food consumption in treatment trials for mice in each of the four experimental groups based upon the quantity of food eaten (grams/days/group). Food eaten by the diabetic mice in the two treatment groups were significantly greater than those eaten by the Diabetic Control mice during the last 12 weeks of the study. The double arrows indicate time of diagnosis as diabetic for animals in the group fed the diabetic induction diet (within 8 to 9 weeks from the start of the trial). Mean values are indicated by symbols and vertical bars to indicate possible variation of the values at each interval.

Figure 2:
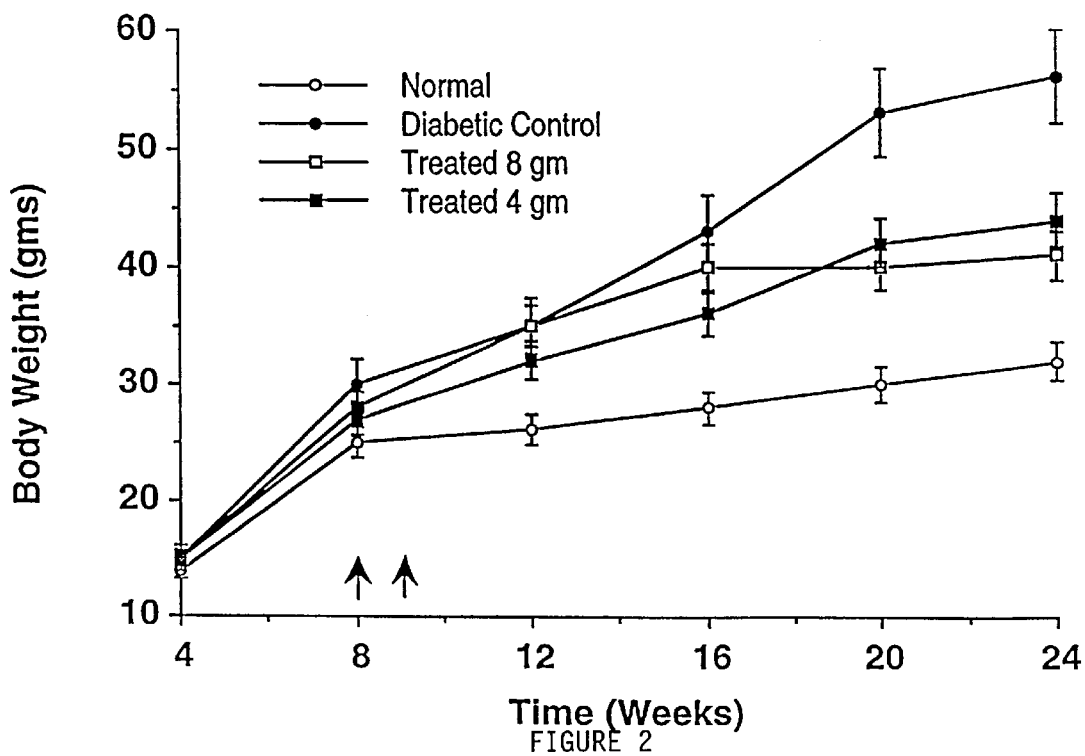
FIG. 2 is a chart representing body weights of mice in treatment trials.

In contrast to the pattern of increased food consumption for the two groups of diabetic mice treated with 4 grams or 8 grams respectively, body weights of these two subject groups were significantly lower than the body weight of the Diabetic Control group of mice during the last 8 weeks of the trials (see FIG. 2). Again, the double arrows indicate the time of diagnosis as diabetic for the animals in the control group fed the diabetic induction diet. Again, mean values are indicated by symbols and vertical bars indicate possible variation of values at each interval.

Figure 3:
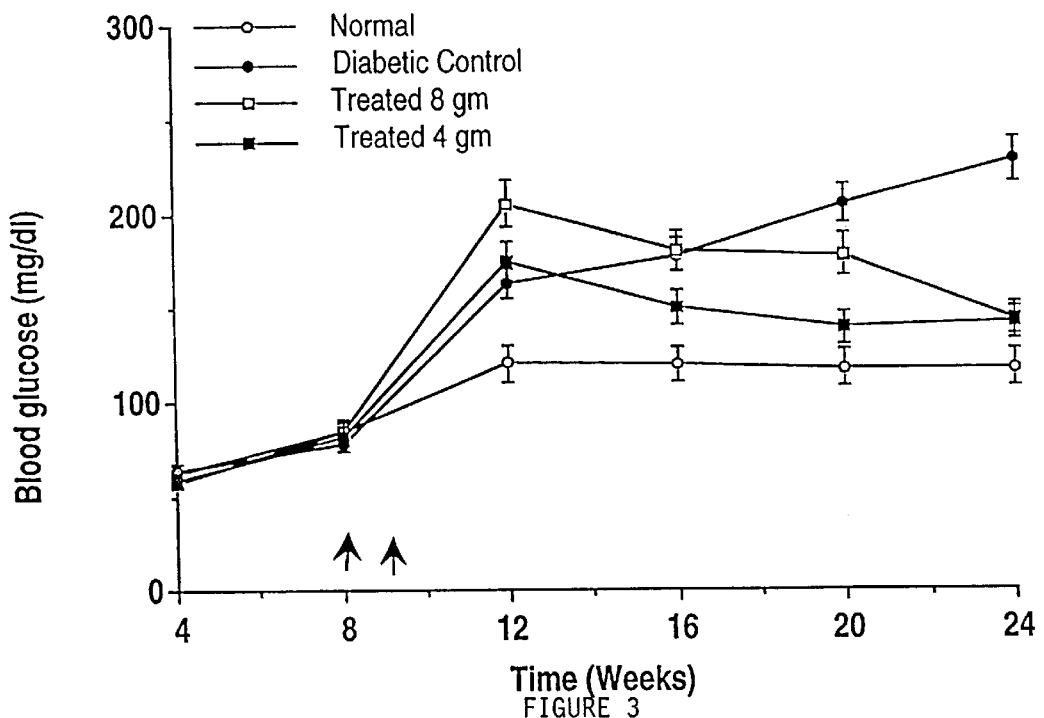
FIG. 3 represents blood glucose levels of mice in treatment trials.

Blood glucose levels were found to significantly rise in all three of the experimental groups fed diabetes induction diets during the time between 7 and 9 weeks of the trial (see FIG. 3). Peak blood glucose values were detected for all three groups at 12 weeks of the trial. Thereafter, the levels of blood glucose in the two Treated groups (4 grams and 8 grams) declined slowly, but significantly, from those of the Diabetes Control group for the remainder of the trial. Toward the end, the Treated groups almost reached the normal values as the Normal mice. This is a result which was originally unexpected. While most of the herbal ingredients are known to be slightly effective in the treatment of NIDDM, this alone does not account for these results. These results are not indicative of a mere expected cumulative effect of the various herbals being used to treat NIDDM. Rather, the herbal formulation provides a vastly more effective treatment than the sum of individual herbal parts would seem to have initially indicated.

In Vivo Studies—Prevention Trial Results

Figure 4:
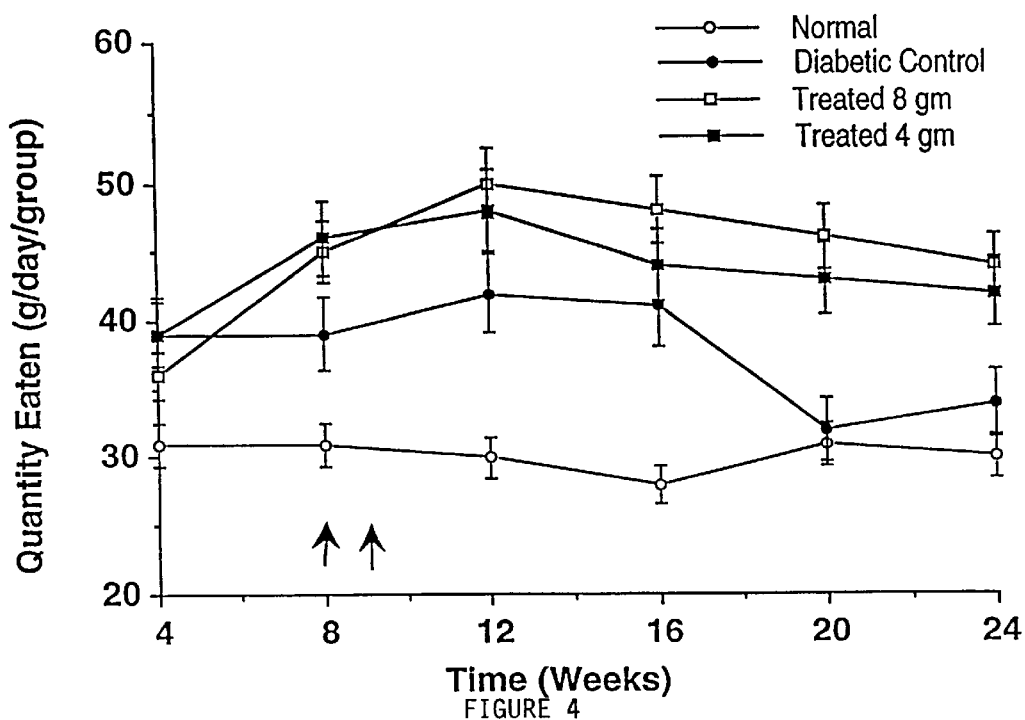
FIG. 4 is a graph representing food consumption by mice in prevention trials.

Referring now to FIG. 4 of the drawings, a pattern of food consumption for animals in each of the four experimental groups of the prevention trials is shown which is based upon quantity of food eaten (grams/days/group). The amount of food eaten by the mice in the two Treatment groups was significantly greater than those eaten by the Diabetic Control mice during the last 8 weeks of the study.

Figure 5:
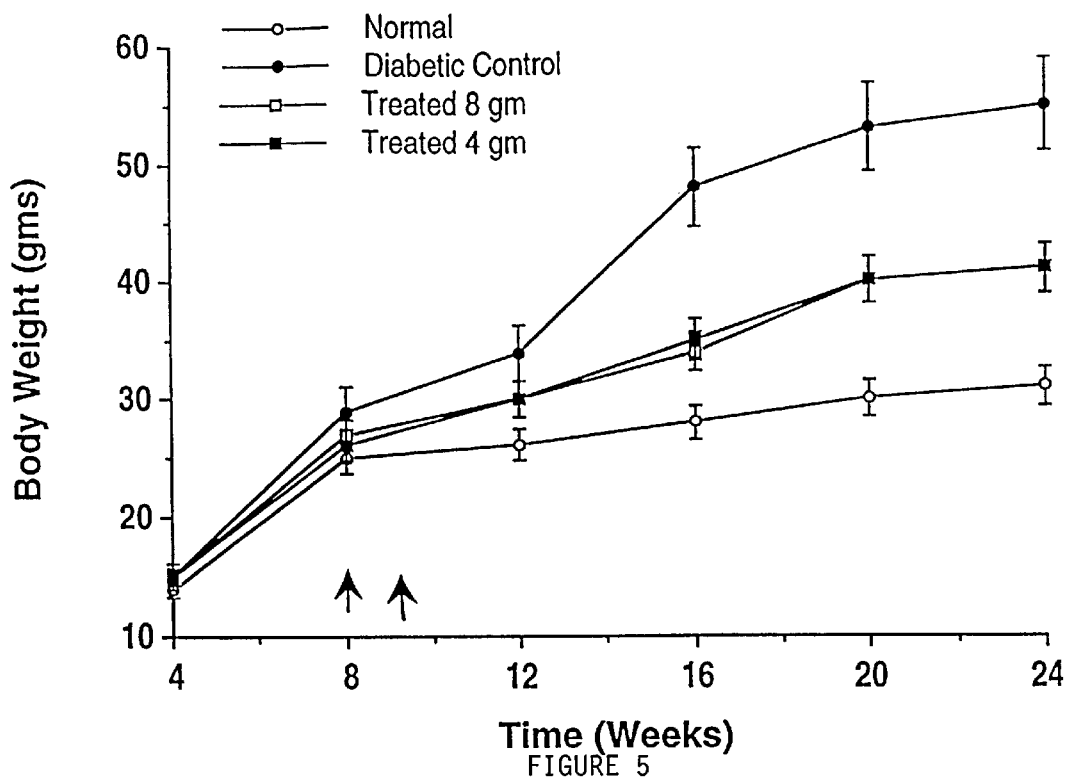
FIG. 5 is a graph representing body weights of mice in prevention trials.

In contrast with the pattern of increased food consumption seen in the two groups of diabetic mice treated in FIG. 4, body weights of the subject of those two Treated groups was significantly lower than those of the Diabetic Control group from 12 to 24 weeks of the trials (See FIG. 5). Again, the double arrows indicate the time of diagnosis of the mice as being diabetic.

Figure 6:
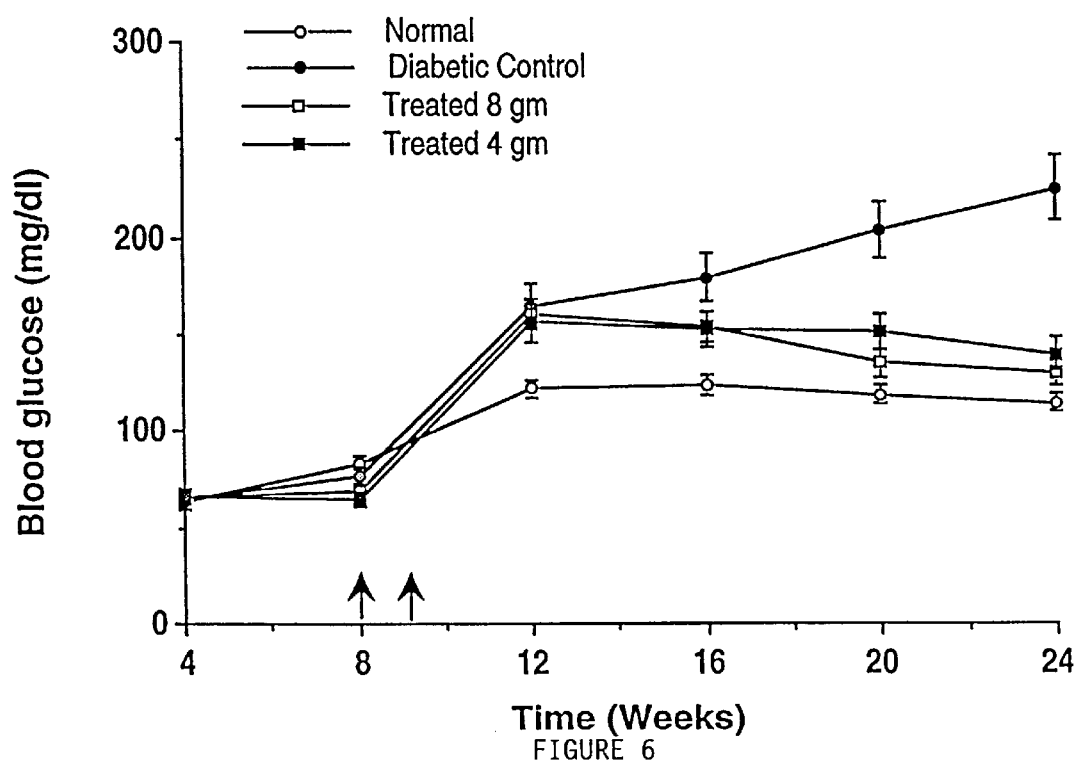
FIG. 6 is a graph representing blood glucose levels of mice in prevention trials.
Figure 7:
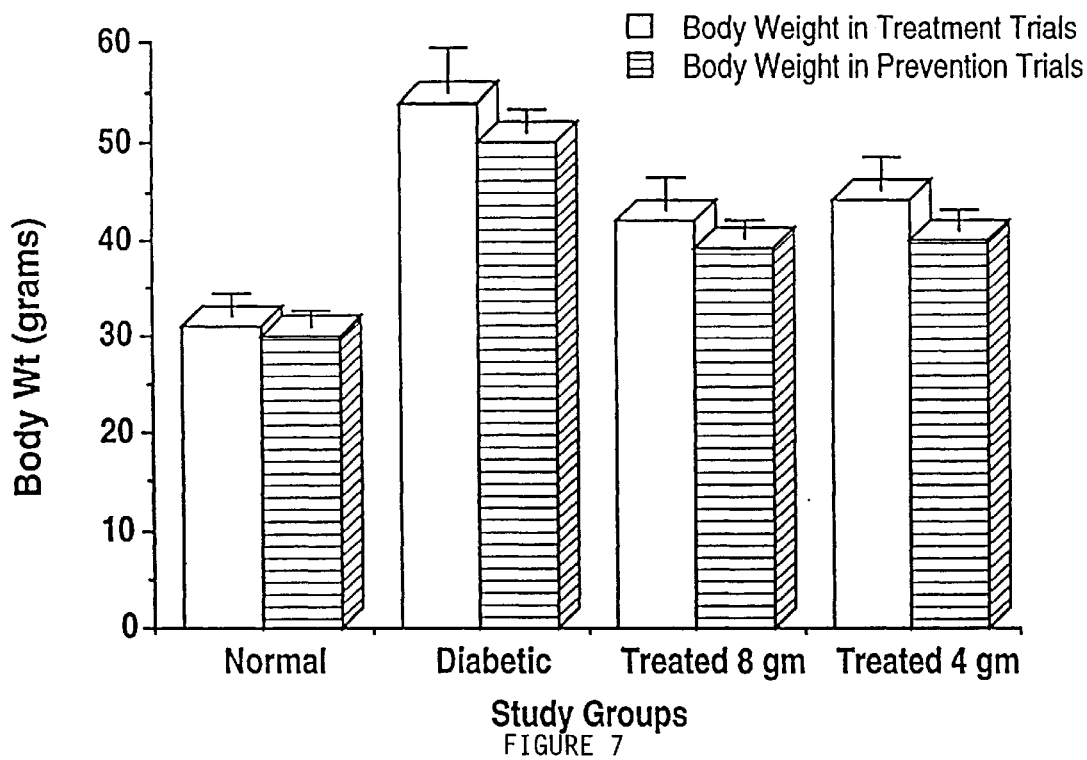
FIG. 7 is a summary of body weight of mice at the end of trials.

The blood glucose levels had a marked increase for all three of the experimental groups fed a diabetes induction diet during the first 7 to 9 weeks of the trial (see FIG. 6). The peak blood glucose values (other than for the Diabetic Control group) was the maximum for all three groups at week 12 in the trial. Thereafter, the blood glucose level of the two treated groups declined significantly from those of the Diabetes Control group during the remainder of the trial. At the end of the trial, the two Treated groups were almost normal in their blood glucose levels. Again, the herbal formulation provides a vastly more effective preventative measure than the sum of individual herbal parts would seem to have initially indicated.

In Vivo Studies—Treatment and Prevention Trials

Figure 12:
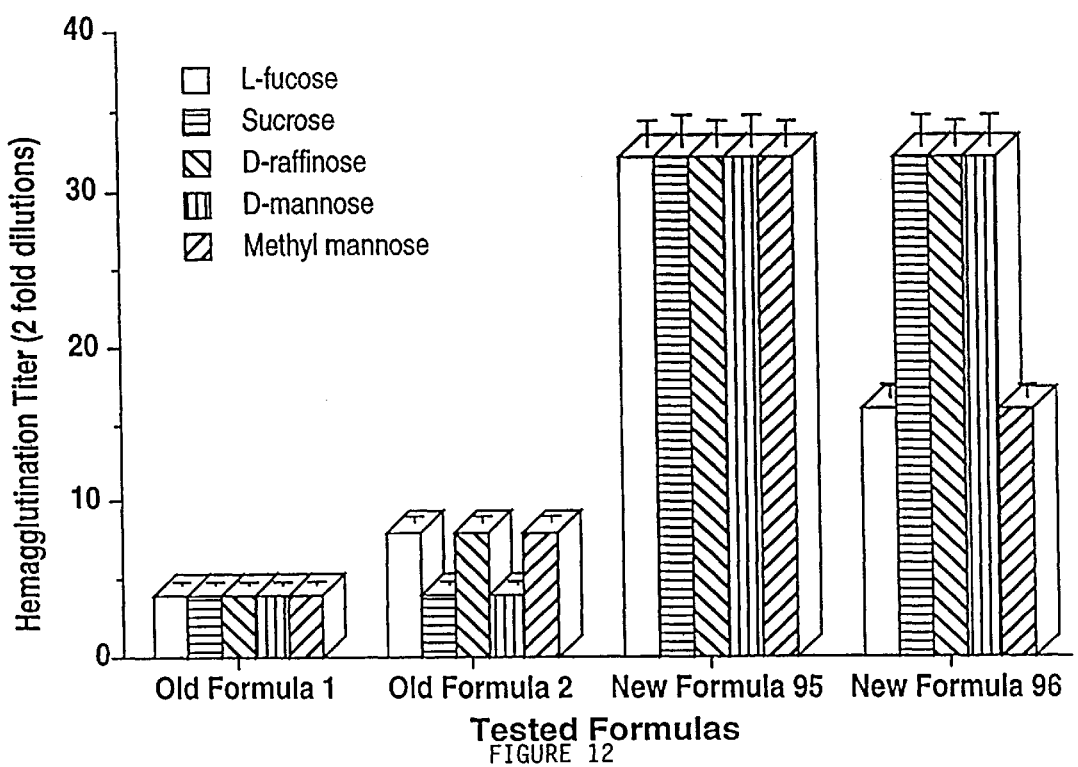
FIG. 12 is a summary of sugar binding titers of lectins in old and new mixtures.

A series of charts are used to summarize the body weight, blood glucose, serum insulin, and insulin resistance for each of the groups of mice at the end of 24 weeks. Such summaries are illustrated in FIGS. 7 through 10 of the treatment and prevention trials. FIG. 12 gives a comparison of the body weight of each experimental group in the treatment and prevention trials. Body weights of subjects that were in the group that received the present invention, whether through prevention trial or treatment trial, were significantly lower than those measured in the diabetic control group at the 24 week period of the trial. The degree of this significance is greater than the expected cumulative effect of the various herbals. The preferred formula provides a means of treatment and prevention which is vastly more effective than would be the expected result of combining the individual herbals. This is further established when examining the in vitro trial results which compare old formulations and their results in comparison to the results obtainable with the new formulation.

Figure 8:
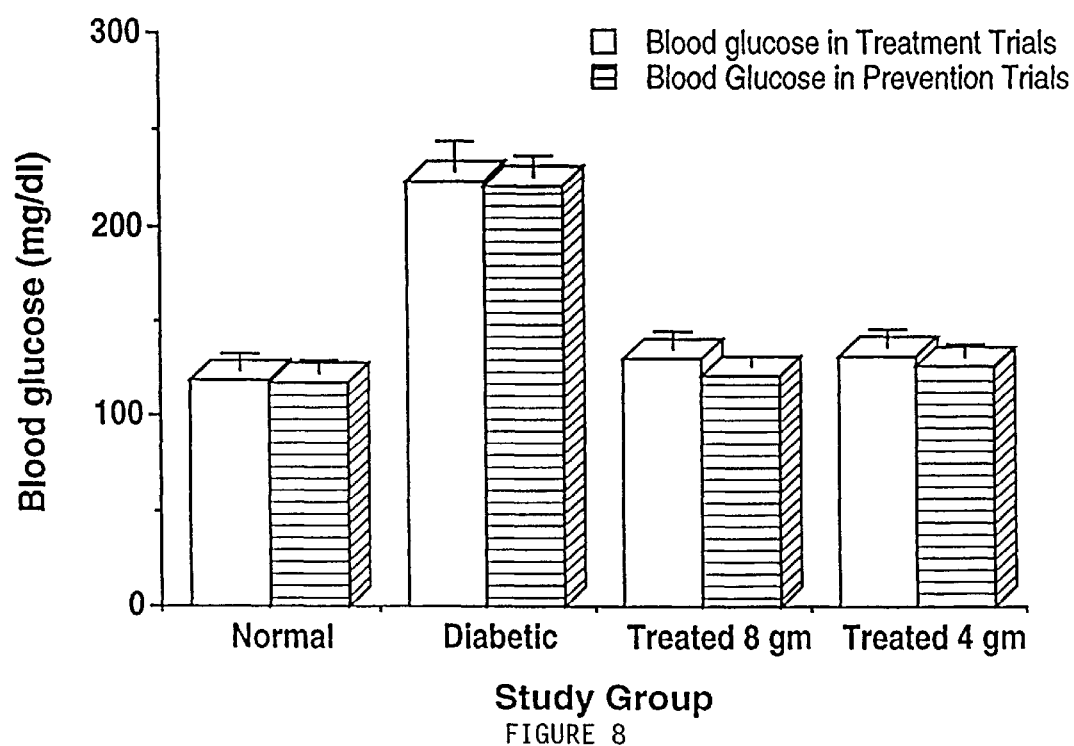
FIG. 8 is a summary of blood glucose levels of mice at the end of trials.
Figure 9:
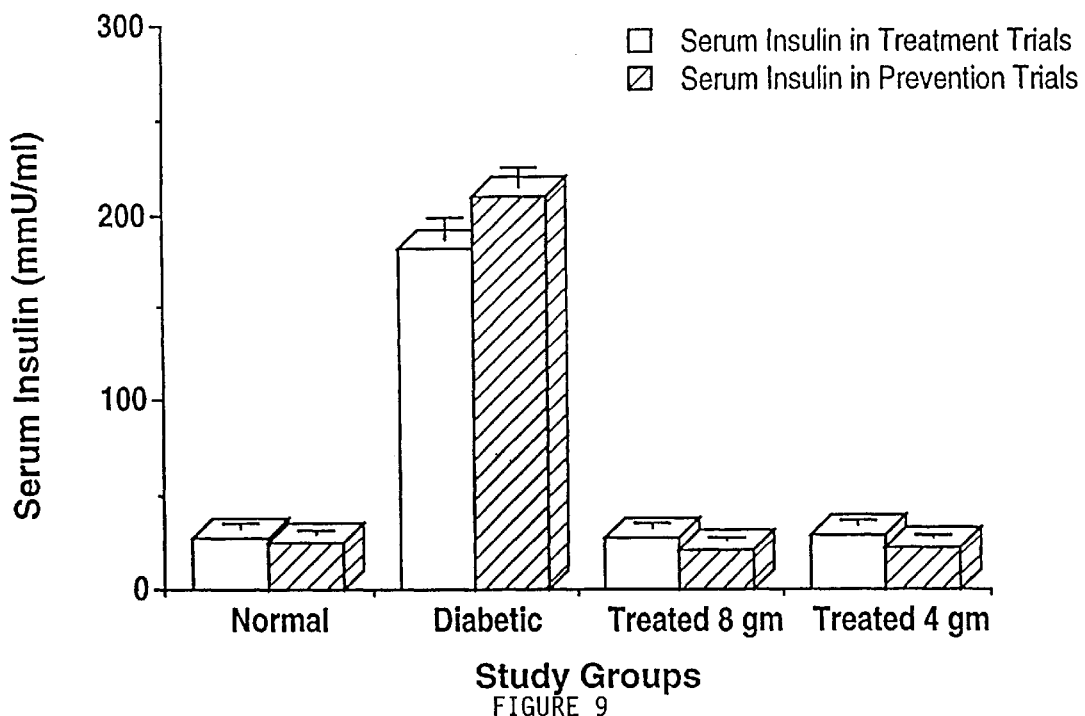
FIG. 9 is a summary of serum insulin levels of mice at the end of trials.

Blood glucose levels of the mice in the groups that received the present formula, whether during the prevention trial or during the treatment trial, were significantly lower than those measured in the Diabetic Control group at the 24 week period (see FIG. 8). The overall levels in the blood glucose measurement was not significantly different from those measured in the normal control group.

Serum insulin levels for the mice in the various groups were also measured at the 24 week period. The groups that received the present formula, whether during the prevention trial or during the treatment trial, were significantly lower than those of the Diabetic Control group at the end of 24 weeks (see FIG. 9). The serum insulin level for the mice receiving treatment were not significantly different than those in the Normal Control group. There was a very significant difference between the Diabetic Control group.

Figure 10:
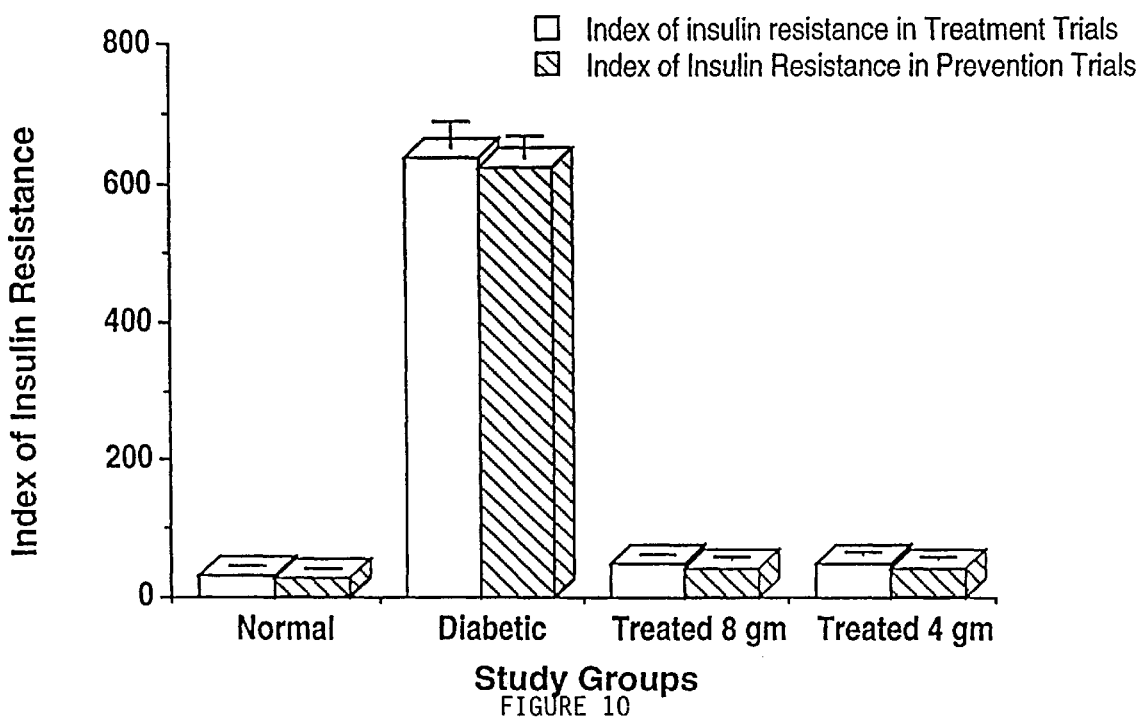
FIG. 10 is a summary of index of the insulin resistance levels of mice at the end of trials.

A summary of the index of insulin resistence levels was also measured at the end of 24 weeks as can be seen in FIG. 10. The mice that received the treatment, whether during a prevention trial or a treatment trial, were significantly lower than those in the Diabetic Control group at the end of 24 weeks. Again, this significance is greater than what would be expected from combining the herbals. Also, the mice receiving the treatment or prevention were not significantly different than those in the Normal Control group.

In Vitro Studies—Finding of Lectins in Present Invention with Reference Sugars

Figure 11:
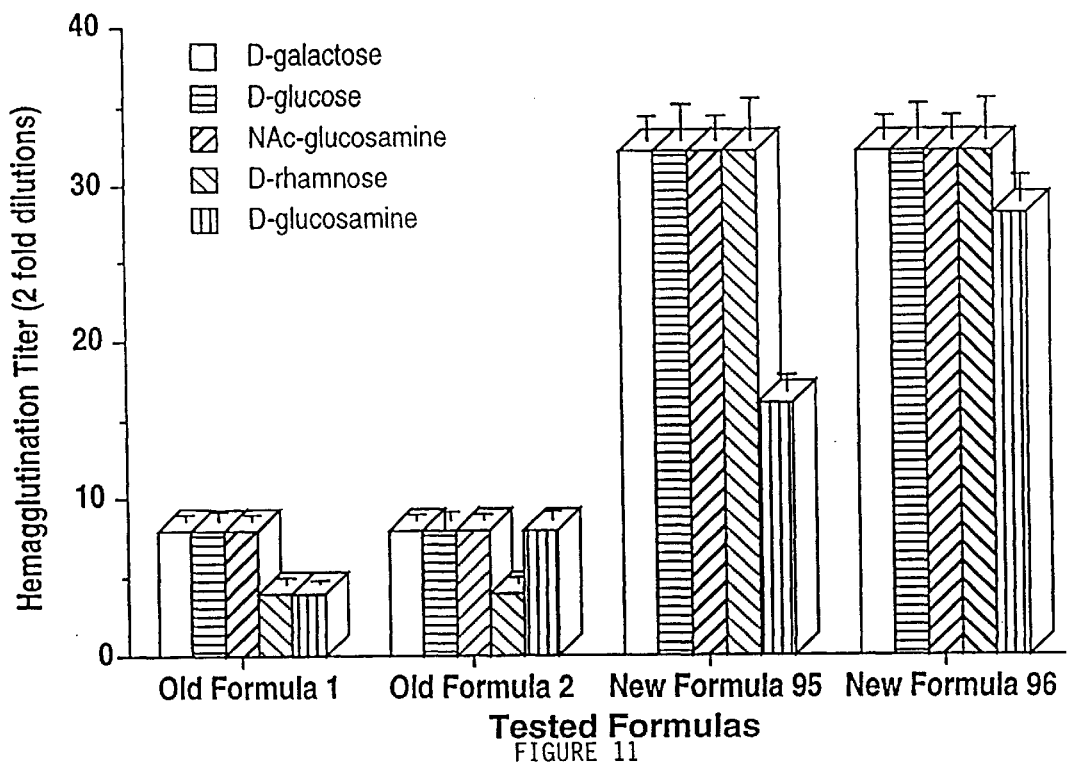
FIG. 11 is a summary of sugar binding titers of lectins in old and new mixtures.
Figure 13:
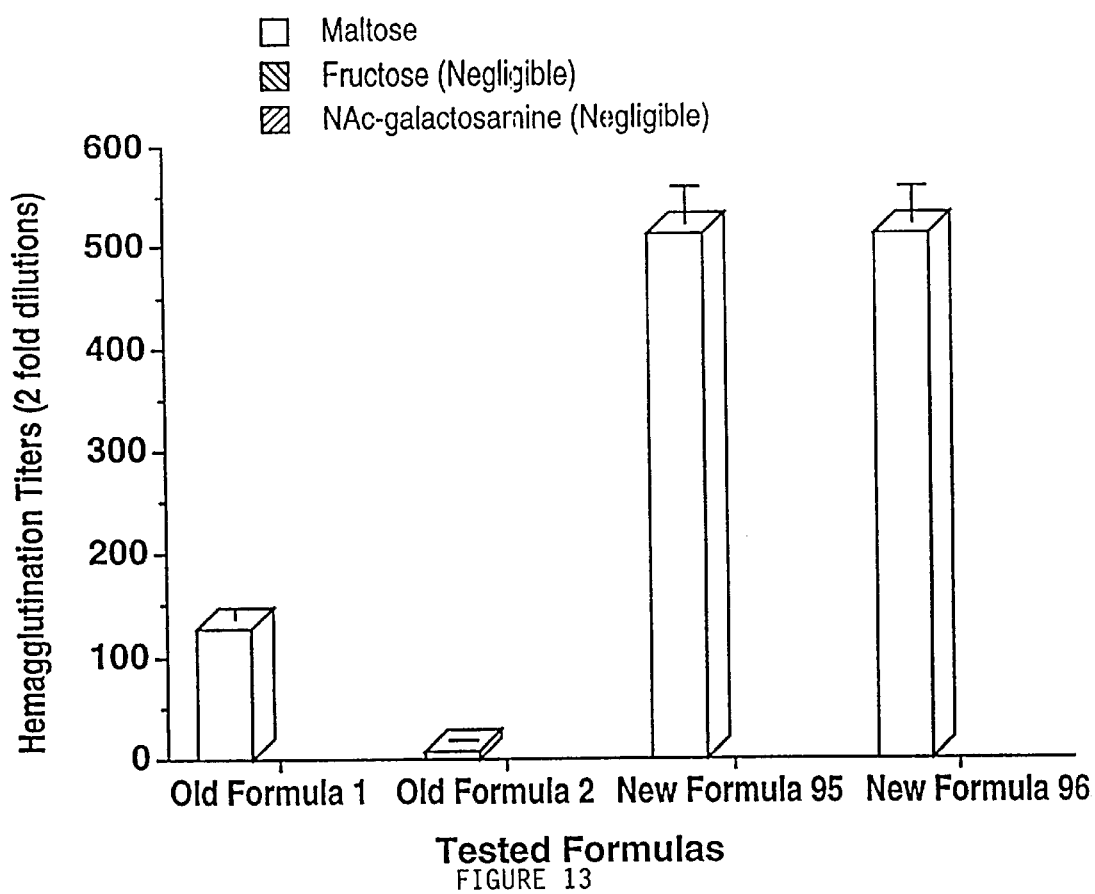
FIG. 13 is a summary of sugar binding titers of lectins in old and new formulas.

In attempting to establish the range of specificity and sensitivity of the lectin-like agglutinins detected in the extract of the formula of the present invention by hemagglutination assays, sugar binding hemagglutination assays were used. In these assays, 13 different sugars, ranging from simple sugars to disaccharides, were ultimately tested for binding with the extract of the new formula, which is illustrated in FIGS. 11 through 13. The results of the sugar binding studies showed that while extracts under the present formula and under the old formulations of Drs. Huo & Lo, designated Formula One and Formula Two respectively, all showed the presence of agglutinins with individual sugars. The levels (titers) of the specific sugar binding hemagglutin were significantly and markedly higher using extracts of the present formula for all reference sugars tested (see FIGS. 11–13). As shown by these results, the degree of sugar binding obtained by the present formula vastly exceeds the old formulas. In fact, if the results of the old formulas are combined, they still would not approach the level of sugar binding which has occurred with the new formula.

Sugar binding titers of extracted material of Formulas One and Two were lowest when tested against D-galactose, D-glucose, NAc-glucosamine, D-rhamnose, D-glucosamine, L-fucose, Sucrose, D-raffinose, D-mannose, Methyl mannose, and Maltose. Also, the materials tested were non-reactive with fructose and NAc-galactosamine. The new formulations were also non-reactive with fructose and NAc-galactosamine.

Applicants have done toxicity studies of the above herbal formulation. No significant toxicity was recorded in animals even though the animals were fed huge diets of the herbal formulation. The amount of the herbal formulation in excess of the amount required for treatment appeared to give nutritional value to the subject test animals. However, because the herbal formulation is still being experimented with, there are certain precautions that should be taken. Extremely large amounts will affect the digestive system and may show itself as diarrhea. Until there is further experimentation, the herbal formulation should not be used by (a) pregnant women, (b) persons with allergic conditions, (c) individuals with kidney problems, (d) persons on dialysis or other extra-corporal liquid supplementation, and (e) persons with compromised immune systems.

What is claimed is:

1. A dietary supplement for the treatment of non-insulin dependent diabetes mellitus, said supplement comprising the following plant components:

Radix ginseng, Radix rehmanniae, Radix ophiopogonis, Fructus schisandrae, Rhizoma dioscoreae, Radix astragali, Radix trichosanthis, Radix puerariae, Fructus lycii, Scleorotium poria cocos, Rhizoma alismatis, Rhizoma coptidis, Fructus rubi, Radix scutellariae, and Radix glycyrrhizae, whereby the dietary supplement is prepared by combining hot-water extracts from the following dried components: Radix trichosanthis, Fructus lycii, Radix rehmanniae, Radix astragali, Rhizoma alismatis, Fructus rubi, Sclerotium poria cocos, Fructus schisandrae, and Radix ophiopogonis, with milled powders of the following dried components: Rhizoma dioscoreae, Radix ginseng, Radix puerariae, Radix glycyrrhizae, Radix scutellariae, and Rhizoma coptidis, in amounts effective to treat non-insulin dependent diabetes mellitus.

2. A supplement according to claim 1, comprising the following amounts of said dried components:

Radix trichosanthis: in the range of about 100 g up to about 400 g;

Fructus lycii: in the range of about 100 g up to about 400 g;

Radix rehmanniae: in the range of about 125 g up to about 500 g;

*Radix astragali*: in the range of about 100 g up to about 400 g;

*Rhizoma alismatis*: in the range of about 75 g up to about 300 g;

*Fructus rubi*: in the range of about 50 g up to about 200 g;

*Sclerotium poria cocos*: in the range of about 75 g up to about 300 g;

*Fructus schisandrae*: in the range of about 100 g up to about 400 g;

*Radix ophiopogonis*: in the range of about 100 g up to about 400 g;

*Rhizoma dioscoreae*: in the range of about 100 g up to about 400 g;

*Radix ginseng*: in the range of about 125 g up to about 500 g;

*Radix puerariae*: in the range of about 100 g up to about 400 g;

*Radix glycyrrhizae*: in the range of about 25 g up to about 100 g;

*Radix scutellariae*: in the range of about 25 g up to about 100 g; and

*Rhizoma coptidis*: in the range of about 50 g up to about 200 g.

3. A supplement according to claim 1, comprising the following amounts of said dried components:

*Radix trichosanthis*: about 200 g;

*Fructus lycii*: about 200 g;

*Radix rehmanniae*: about 250 g;

*Radix astragali*: about 200 g;

*Rhizoma alismatis*: about 150 g;

*Fructus rubi*: about 100 g;

*Sclerotium poria cocos*: about 150 g;

*Fructus schisandrae*: about 200 g;

*Radix ophiopogonis*: about 200 g;

*Rhizoma dioscoreae*: about 200 g;

*Radix ginseng*: about 250 g;

*Radix puerariae*: about 200 g;

*Radix glycyrrhizae*: about 50 g;

*Radix scutellariae*: about 50 g; and

*Rhizoma coptidis*: about 100 g.

4. A supplement according to claim 1, wherein the dietary supplement comprises the following amounts of each dried component:

*Radix trichosanthis*: in the range of about 4% up to about 16%;

*Fructus lycii*: in the range of about 4% up to about 16%;

*Radix rehmanniae*: in the range of about 5% up to about 20%;

*Radix astragali*: in the range of about 4% up to about 16%;

*Rhizoma alismatis*: in the range of about 3% up to about 12%;

*Fructus rubi*: in the range of about 2% up to about 8%;

*Sclerotium poria cocos*: in the range of about 3% up to about 12%;

*Fructus schisandrae*: in the range of about 4% up to about 16%;

*Radix ophiopogonis*: in the range of about 4% up to about 16%;

*Rhizoma dioscoreae*: in the range of about 4% up to about 16%;

*Radix ginseng*: in the range of about 5% up to about 20%;

*Radix puerariae*: in the range of about 4% up to about 16%;

*Radix glycyrrhizae*: in the range of about 1% up to about 4%;

*Radix scutellariae*: in the range of about 1% up to about 4%; and

*Rhizoma coptidis*: in the range of about 2% up to about 8%, wherein all percent values are on a weight percent basis relative to the total weight of all dried components.

5. A supplement according to claim 1, wherein each plant component is obtained from the corresponding plant as follows:

| Component | Plant |
| --- | --- |
| *Radix trichosanthis*: | *Tricosanthes kirilowii*; |
| *Fructus lycii*: | *Lycium bararum*; |
| *Radix rehmanniae*: | *Rhemanniae glutinosa*; |
| *Radix astragali*: | *Astragalus membranaceus*; |
| *Rhizoma alismatis*: | *Alisma orientalis*; |
| *Fructus rubi*: | *Rubus chingii*; |
| *Sclerotium poria cocos*: | *Poria cocos*; |
| *Fructus schisandrae*: | *Schisandra chinensis*; |
| *Radix ophiopogonis*: | *Ophiopogon japonicus*; |
| *Rhizoma dioscoreae*: | *Dioscorea opposita*; |
| *Radix ginseng*: | *Panax ginseng*; |
| *Radix puerariae*: | *Pueraria lobata*; |
| *Radix glycyrrhizae*: | *Glycyrrhiza uralensis*; |
| *Radix scutellariae*: | *Scutellaria baicalensis*; |
| *Rhizoma coptidis*: | *Coptis chinensis*. |

6. A method of treating non-insulin dependent diabetes mellitus, said method comprising orally administering the dietary supplement according to claim 1 for a suitable period of time.

7. A method of treating non-insulin dependent diabetes mellitus, said method comprising orally administering the dietary supplement according to claim 2 for a suitable period of time.

8. A method of treating non-insulin dependent diabetes mellitus, said method comprising orally administering the dietary supplement according to claim 3 for a suitable period of time.

9. A method of treating non-insulin dependent diabetes mellitus, said method comprising orally administering the dietary supplement according to claim 4 for a suitable period of time.

10. A method of treating non-insulin dependent diabetes mellitus, said method comprising orally administering the dietary supplement according to claim 5 for a suitable period of time.

11. A method of controlling the body weight of a patient having diabetes mellitus, said method comprising orally administering the dietary supplement according to claim 1 for a suitable period of time.

12. A method of controlling the body weight of a patient having diabetes mellitus, said method comprising orally administering the dietary supplement according to claim 2 for a suitable period of time.

13. A method of controlling the body weight of a patient having diabetes mellitus, said method comprising orally administering the dietary supplement according to claim 3 for a suitable period of time.

14. A method of controlling the body weight of a patient having diabetes mellitus, said method comprising orally administering the dietary supplement according to claim 4 for a suitable period of time.

15. A method of controlling the body weight of a patient having diabetes mellitus, said method comprising orally administering the dietary supplement according to claim 5 for a suitable period of time.

16. A method of preparing a dietary supplement for use in treating non-insulin dependent diabetes mellitus, said method comprising:

combining hot-water extracts from the following dried components: *Radix trichosanthis, Fructus lycii, Radix rehmanniae, Radix astragali, Rhizoma alismatis, Fructus rubi, Sclerotium poria cocos, Fructus schisandrae,* and *Radix ophiopogonis* with milled powders of the following dried components: *Rhizoma dioscoreae, Radix ginseng, Radix puerariae, Radix glycyrrhizae, Radix scutellariae,* and *Rhizoma coptidis,* in amounts effective to produce a supplement useful for the treatment of non-insulin dependent diabetes mellitus.

17. A method according to claim 16, comprising the following amounts of said dried components:

*Radix trichosanthis*: in the range of about 100 g up to about 400 g;

*Fructus lycii*: in the range of about 100 g up to about 400 g;

*Radix rehmanniae*: in the range of about 125 g up to about 500 g;

*Radix astragali*: in the range of about 100 g up to about 400 g;

*Rhizoma alismatis*: in the range of about 75 g up to about 300 g;

*Fructus rubi*: in the range of about 50 g up to about 200 g;

*Sclerotium poria cocos*: in the range of about 75 g up to about 300 g;

*Fructus schisandrae*: in the range of about 100 g up to about 400 g;

*Radix ophiopogonis*: in the range of about 100 g up to about 400 g;

*Rhizoma dioscoreae*: in the range of about 100 g up to about 400 g;

*Radix ginseng*: in the range of about 125 g up to about 500 g;

*Radix puerariae*: in the range of about 100 g up to about 400 g;

*Radix glycyrrhizae*: in the range of about 25 g up to about 100 g;

*Radix scutellariae*: in the range of about 25 g up to about 100 g; and

*Rhizoma coptidis*: in the range of about 50 g up to about 200 g.

18. A method according to claim 16, comprising the following amounts of said dried components:

*Radix trichosanthis*: about 200 g;

*Fructus lycii*: about 200 g;

*Radix rehmanniae*: about 250 g;

*Radix astragali*: about 200 g;

*Rhizoma alismatis*: about 150 g;

*Fructus rubi*: about 100 g;

*Sclerotium poria cocos*: about 150 g;

*Fructus schisandrae*: about 200 g;

*Radix ophiopogonis*: about 200 g;

*Rhizoma dioscoreae*: about 200 g;

*Radix ginseng*: about 250 g;

*Radix puerariae*: about 200 g;

*Radix glycyrrhizae*: about 50 g;

*Radix scutellariae*: about 50 g; and

*Rhizoma coptidis*: about 100 g.

19. A method according to claim 16, comprising the following amounts of said dried components:

*Radix trichosanthis*: in the range of about 4% up to about 16%;

*Fructus lycii*: in the range of about 4% up to about 16%;

*Radix rehmanniae*: in the range of about 5% up to about 20%;

*Radix astragali*: in the range of about 4% up to about 16%;

*Rhizoma alismatis*: in the range of about 3% up to about 12%;

*Fructus rubi*: in the range of about 2% up to about 8%;

*Sclerotium poria cocos*: in the range of about 3% up to about 12%;

*Fructus schisandrae*: in the range of about 4% up to about 16%;

*Radix ophiopogonis*: in the range of about 4% up to about 16%;

*Rhizoma dioscoreae*: in the range of about 4% up to about 16%;

*Radix ginseng*: in the range of about 5% up to about 20%;

*Radix puerariae*: in the range of about 4% up to about 16%;

*Radix glycyrrhizae*: in the range of about 1% up to about 4%;

*Radix scutellariae*: in the range of about 1% up to about 4%; and

*Rhizoma coptidis*: in the range of about 2% up to about 8%, wherein all percent values are on a weight percent basis relative to the total weight of all dried components.

* * * * *